US00PP24002P2

(12) United States Plant Patent
Hartman

(10) Patent No.: US PP24,002 P2
(45) Date of Patent: Oct. 22, 2013

(54) ***CALADIUM* PLANT NAMED 'PARTY PUNCH'**

(50) Latin Name: *Caladium×hortulanum*
Varietal Denomination: Party Punch

(76) Inventor: Robert Dale Hartman, Lake Placid, FL (US)

( * ) Notice: Subject to any disclaimer, the term of this patent is extended or adjusted under 35 U.S.C. 154(b) by 109 days.

(21) Appl. No.: 13/374,460

(22) Filed: Dec. 29, 2011

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — June Hwu
(74) *Attorney, Agent, or Firm* — C. A. Whealy

(57) ABSTRACT

A new and distinct cultivar of *Caladium* plant named 'Party Punch', characterized by its upright and somewhat mounding plant habit; intermediate plant size; uniform plant habit; vigorous and dense growth habit; fancy-type leaves with dark red-colored venation, greyed purple-colored interveinal areas with light and dark red purple-colored spots and surrounded with dark green-colored borders; and good landscape performance.

4 Drawing Sheets

Botanical designation: *Caladium×hortulanum.*
Cultivar denomination: 'PARTY PUNCH'.

CROSS-REFERENCED TO CLOSELY-RELATED APPLICATIONS

Title: *Caladium* plant named 'Bombshell'.
Applicant: Robert Dale Hartman.
Filed: Dec. 29, 2011.
Ser. No.: Filed concurrently with this application (U.S. Plant patent application Ser. No. 13/374,456).

BACKGROUND OF THE INVENTION

The present invention relates to a new and distinct cultivar of *Caladium* plant, botanically known as *Caladium×hortulanum*, commercially referred to as a fancy leaf-type *Caladium* and hereinafter referred to by the name 'Party Punch'.

The objective of the Inventor's breeding program is to create new *Caladium* plants that have uniform plant habit, exceptional container and garden performance and attractive foliage coloration.

The new *Caladium* plant originated from a cross-pollination made by the Inventor in April, 2007, in Avon Park, Fla. of a proprietary selection of *Caladium×hortulanum* identified as code number WS-03-36, not patented, as the female, or seed, parent with *Caladium×hortulanum* 'Red Flash', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2008.

Asexual reproduction of the new *Caladium* plant by 'chipping' the tubers (cutting the tuber into segments, each segment containing an axillary bud and tuber cortical tissue) in a controlled outdoor nursery environment in Lake Placid, Fla. since April, 2009 has shown that the unique features of this new *Caladium* plant are stable and reproduced true to type in successive generations of asexual reproduction.

SUMMARY OF THE INVENTION

Plants of the new *Caladium* have not been observed under all possible environmental conditions and cultural practices.

The phenotype may vary somewhat with variations in environmental conditions such as temperature and light intensity, without, however, any variance in genotype.

The following traits have been repeatedly observed and are determined to be the unique characteristics of 'Party Punch'. These characteristics in combination distinguish 'Party Punch' as a new and distinct *Caladium* plant:

1. Upright and somewhat mounding plant habit; intermediate plant size.
2. Uniform plant habit.
3. Vigorous and dense growth habit.
4. Fancy-type leaves with dark red-colored venation, greyed purple-colored interveinal areas with light and dark red purple-colored spots and surrounded with dark green-colored borders.
5. Good landscape performance.

Plants of the new *Caladium* differ primarily from plants of the female parent selection in the following characteristics:

1. Plants of the new *Caladium* are taller than and not as mounding as plants of the female parent selection.
2. Leaves of plants of the new *Caladium* are ovate in shape whereas leaves of plants of the female plant selection are lanceolate in shape.
3. Leaf margins of plants of the new *Caladium* are not as undulate as leaf margins of plants of the female parent selection.
4. Plants of the new *Caladium* and the female parent selection differ in leaf coloration as leaves of plants of the female parent selection have pink-colored centers, rose pink-colored primary venation, green and white-colored interveinal areas and dark green-colored borders.

Plants of the new *Caladium* differ primarily from plants of the male parent, 'Red Flash', in the following characteristics:

1. Plants of the new *Caladium* are shorter than and not as upright as plants of 'Red Flash'.
2. Plants of the new *Caladium* grow faster than plants of 'Red Flash'.
3. Plants of the new *Caladium* and 'Red Flash' differ in leaf coloration as leaves of plants of 'Red Flash' have red-colored venation and interveinal areas with pink-colored spots and dark green-colored background and borders.

Plants of the new *Caladium* can be compared to plants of 'Bombshell', disclosed in a U.S. Plant Patent application filed concurrently. Plants of the new *Caladium* are more mounding than plants of 'Bombshell'. In addition, plants of the new *Caladium* and 'Bombshell' differ in leaf petiole and leaf coloration.

Plants of the new *Caladium* can be compared to plants of *Caladium* 'Rosebud', not patented. In side-by-side comparisons conducted in Avon Park, Fla., plants of the new *Caladium* differed primarily from plants of 'Rosebud' in the following characteristics:

1. Plants of the new *Caladium* were taller and more upright than plants of 'Rosebud'.
2. Plants of the new *Caladium* grew slower than plants of 'Rosebud'.
3. Plants of the new *Caladium* and 'Rosebud' differed in leaf coloration as leaves of plants of 'Rosebud' had pink-colored venation and interveinal areas surrounded by whitish-colored areas and green-colored borders.

Plants of the new *Caladium* can also be compared to plants of *Caladium* 'Carolyn Whorton', not patented. In side-by-side comparisons conducted in Avon Park, Fla., plants of the new *Caladium* differed primarily from plants of 'Carolyn Whorton' in the following characteristics:

1. Plants of the new *Caladium* were shorter than and not as upright as plants of 'Carolyn Whorton'.
2. Plants of the new *Caladium* grew faster than plants of 'Carolyn Whorton'.
3. Plants of the new *Caladium* and 'Carolyn Whorton' differed in leaf coloration as leaves of plants of 'Carolyn Whorton' had deep rose red-colored venation with pink-colored blotches and green-colored borders.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Party Punch' grown in a 15-cm container in a shadehouse.

The photograph at the top of the second sheet is a side perspective view of typical plants of 'Party Punch' grown in an outdoor nursery.

The photograph at the bottom of the second sheet is a close-up view of typical freshly-harvested tubers and roots of 'Party Punch'.

The photograph on third sheet is a comparison view of typical plants of 'Party Punch' grown in 15-cm containers, the plant on the left has not had its tuber de-eyed and the plant on the right has had its tuber de-eyed prior to planting.

The photograph at the top of the fourth sheet is a comparison view of typical potted plants of the female parent selection (left), 'Party Punch' (center) and the male parent, 'Red Flash' (right).

The photograph at the bottom of the fourth sheet is a comparison view of typical potted plants of 'Rosebud' (left), 'Party Punch' (center) and 'Carolyn Whorton' (right).

DETAILED BOTANICAL DESCRIPTION

The aforementioned photographs and following observations and measurements describe plants grown during the spring in 15-cm containers in Avon Park, Fla. in a polypropylene-covered shadehouse (30% shade) and plants grown during the autumn in ground beds in an outdoor nursery in Zolfo Springs, Fla. All plants were grown under environmental conditions and cultural practices which approximate those generally used in commercial shadehouse and outdoor nursery *Caladium* production. During the production of the plants, day temperatures ranged from about 29° C. to 33° C. (shadehouse) or 29° C. to 35° C. (outdoor nursery), night temperatures ranged from about 22° C. to 25° C. (shadehouse) or 23° C. to 26° C. (outdoor nursery) and light levels were about 8,000 foot-candles (shadehouse) or 10,000 to 12,000 foot-candles (outdoor nursery). Plants grown in the shadehouse were eight weeks old when the photographs and the detailed description were taken. Plants grown in the outdoor nursery were seven months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Party Punch'.

Parentage:

*Female, or seed, parent.*—Proprietary selection of *Caladium×hortulanum* identified as code number WS-03-36, not patented.

*Male, or pollen, parent.*—*Caladium×hortulanum* 'Red Flash', not patented.

Propagation:

*Type.*—By "chipping" the tubers.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented; individual segments ovate in shape. Height: About 2.8 cm. Diameter: About 4.7 cm. Texture: Thick and starchy; somewhat brittle. Color: Epidermis, freshly harvested, close to 199C to 199D and 200A; epidermis, dried tuber, close to 200A to 200B; interior, close to 2C to 2D and 150D; axillary buds, close to 155B. Root description: Thick, fleshy contractile roots; color, close to 155D. Rooting habit: Few lateral branches; moderately dense.

Plant description:

*Plant type.*—Herbaceous perennial; suitable as a potted plant in containers 15-cm to 25-cm and suitable as a landscape plant in shaded areas.

*Plant and growth habit.*—Upright and somewhat mounding plant habit; intermediate plant size; inverted triangle; vigorous and dense growth habit; rapid growth rate; petioles and leaves arise from one or more growing points on tubers; petioles mostly upright and leaning outwardly with development.

*Plant height, from soil level to top of foliar plane, shadehouse-grown potted plants.*—About 29 cm to 37 cm.

*Plant diameter or spread, shadehouse-grown potted plants.*—About 37 cm to 42 cm.

*Number of clumps per plant, shadehouse-grown potted plants.*—About six from de-eyed tubers.

*Cataphylls, shadehouse-grown potted plants.*—Length: About 5.5 cm to 10.5 cm. Width: About 1.2 cm to 2.2 cm. Shape: Lanceolate to elliptic. Apex: Acute. Base: Sheathing the stem. Color, outer surface: Close to N170D tinged with close to 185D and 182D, stippled and tessellated with close to 199D and tinged with close to 147A to 147B; with development, color becoming closer to 199D and 199A tinged with close to 187A to 187B. Color, inner surface: Close to N155C, outer surface colors and patterns visible.

Foliage description:

*Length, shadehouse-grown potted plants.*—About 17 cm to 23.7 cm.

*Width, shadehouse-grown potted plants (flattened).*—About 12 cm to 16.5 cm.

*Shape.*—Ovate.

*Apex.*—Acuminate to acute.

*Base.*—Sagittate, peltate.

*Margin.*—Entire; mostly flat with broad undulations.

*Texture, upper surface.*—Smooth, glabrous.

*Texture, lower surface.*—Smooth, glabrous; glaucous.

*Venation pattern.*—Pinnate.

*Color, shadehouse-grown potted plants.*—Developing leaves, upper surface: Basal notch: Close to 187A. Midrib and primary venation: Close to 53B. Areas surrounding venation: Close to 185C and 53D. Secondary venation: Close to 147A to 147B. Interveinal areas: Close to 185A, 184A and mottled areas, close to 147B and 194B; random spots, close to 65A. Borders: Close to 147A tinged with close to 137A. Margins: Close to 187A. Developing leaves, lower surface: Basal notch: Close to 187B. Midrib and primary venation: Close to 185A to 185B. Areas surrounding venation: Close to 185C. Interveinal areas: Close to 194D tinged with close to N155D, 191A; random spots, close to 49D. Borders: Close to 191A tinged with close to N186C. Margins: Close to 187A. Fully expanded leaves, upper surface: Basal notch: Close to 187A. Midrib and primary venation: Close to 53A to 53B. Secondary venation: Close to 139A. Interveinal areas: Close to 185A and 185B or mottled 139A and 185C; random spots, close to 59D and 65A. Borders: Close to 147A and 139A. Margins: Close to 187A. Fully expanded leaves, lower surface: Basal notch: Close to 187A. Midrib and primary venation: Close to 185B. Areas surrounding venation: Close to 185B to 185C. Secondary venation: Close to 147B overlain with close to 194D and 158D. Interveinal areas: Close to 189A and 191A and also tinged with close to N186C; random spots, close to 49C to 49D and 56A. Margins: Close to 187A.

*Color, field-grown plants.*—Developing leaves, upper surface: Basal notch: Close to N186C. Midrib and primary venation: Close to 59B to 59C. Areas surrounding venation: Close to 185C. Secondary venation: Close to 147A overlain with close to 192D. Interveinal areas: Random sectors and spots, close to 155C and 192D. Margins: Close to 147A. Developing leaves, lower surface: Basal notch: Close to 187A. Area between basal notch and leaf petiole attachment: Close to 187C. Midrib and primary venation: Close to 182D flecked and streaked with close to 184C. Areas surrounding venation: Close to 184C to 184D. Interveinal areas: Random sectors, close to 191A to 191B, close to 147D tinged with close to 184C, close to 147B to 147D, and close to 147B variably tinged with close to N186C; random spots, close to 192D and 155C. Margins: Close to 147A. Fully expanded leaves, upper surface: Basal notch: Close to N186C. Midrib and primary venation: Close to 184A and 59B. Areas surrounding venation: Darker than 183C. Interveinal areas: Close to 147A and N189A; random spots, flecks and fine speckles, close to 155C, 146A and 147A. Margins: Close to 147A. Fully expanded leaves, lower surface: Basal notch: Close to N187C. Area between basal notch and leaf petiole attachment: Close to 187A to 187B. Midrib and primary venation: Close to 195C and N170D. Areas surrounding venation: Close to 184C. Interveinal areas: Close to 189A variably tinged with close to N186C; random spots, close to 193A and 147C. Margins: Close to 147A.

*Petiole.*—Aspect: Mostly erect, slightly outwardly leaning with development; flexible. Length, shadehouse-grown potted plants: About 24 cm to 29.8 cm. Diameter, distal, shadehouse-grown potted plants: About 4.5 mm to 6 mm. Diameter, proximal, shadehouse-grown potted plants: About 6.5 mm to 10 mm. Color, shadehouse-grown potted plants: Close to N170D or N170D tinged with close to 185D, stippled and tessellated with close to 199B tinged with close to 147A and variably and boldly striped with close to 200A tinged with close to 147A; below the leaf/petiole junction, close to 185D or 185D striped with close to 185B. Wing length, shadehouse-grown potted plants: About 4 cm to 4.7 cm. Wing diameter, shadehouse-grown potted plants: About 5 mm to 8 mm. Wing color, shadehouse-grown potted plants, outer surface: Close to N170D tinged with close to 185D and 182D, stippled and tessellated with close to 199D tinged with close to 147A to 147B. Wing color, shadehouse-grown potted plants, inner surface: Close to 155C, outer surface colors and patterns visible.

Inflorescence description: Inflorescence initiation and development have not been observed on plants of the new *Caladium.*

Disease & pest tolerance/resistance: Plants of the new *Caladium* have been observed to have above average tolerance to *Xanthomonas* Leaf Spot and to have average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and suitable for USDA Hardiness Zones 8A to 11.

It is claimed:

1. A new and distinct *Caladium* plant named 'Party Punch' as illustrated and described.

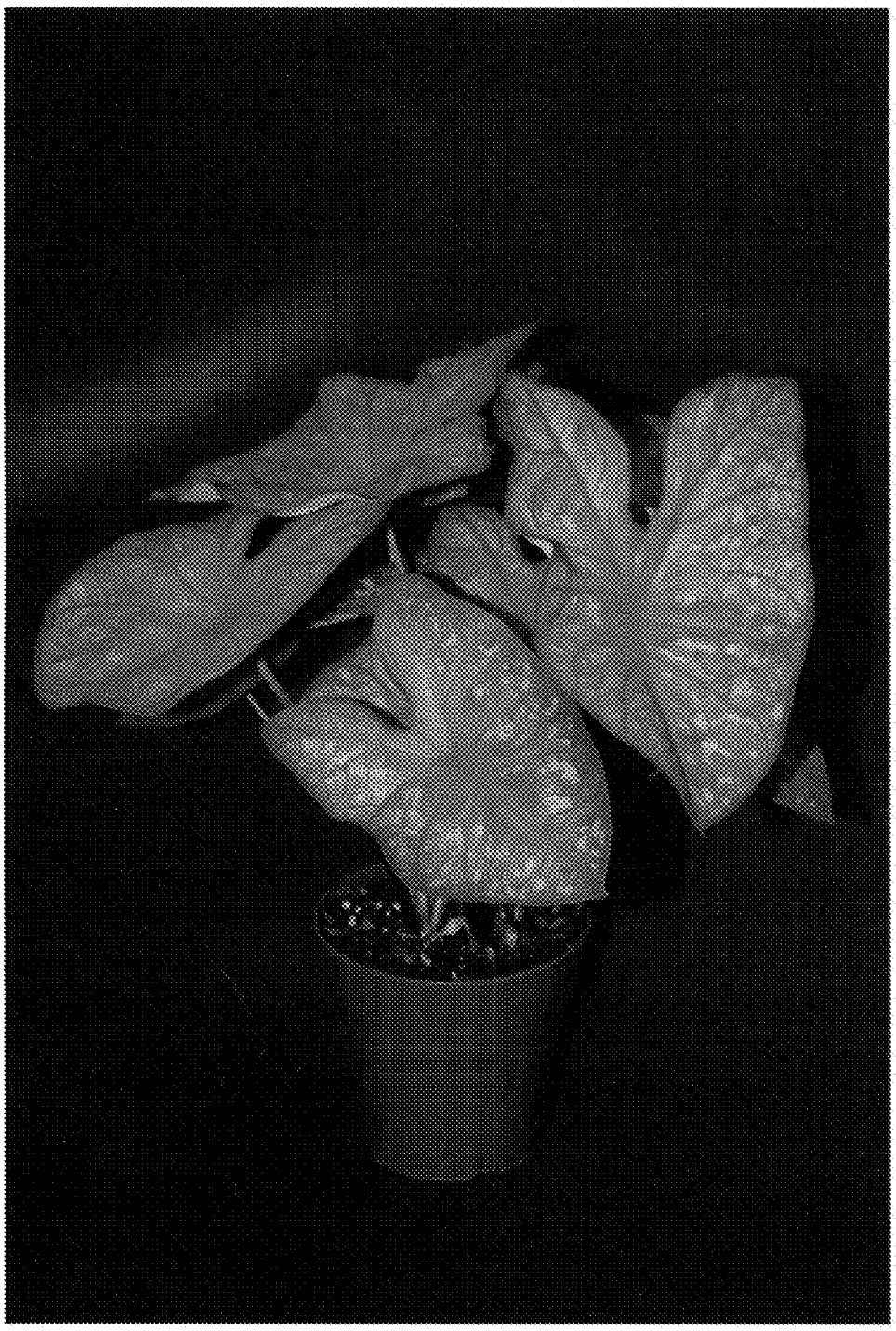

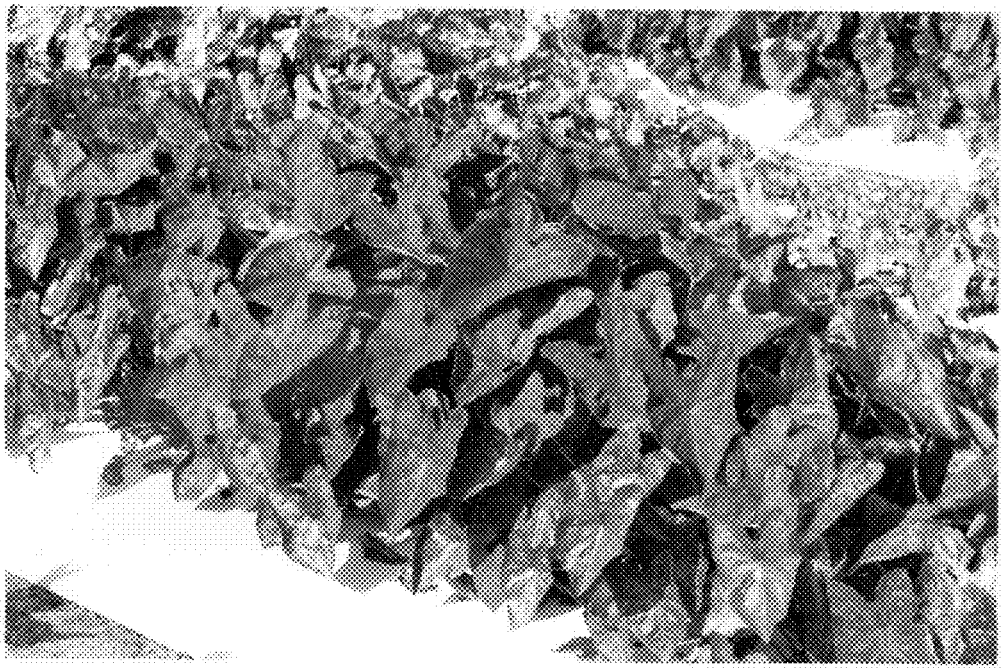
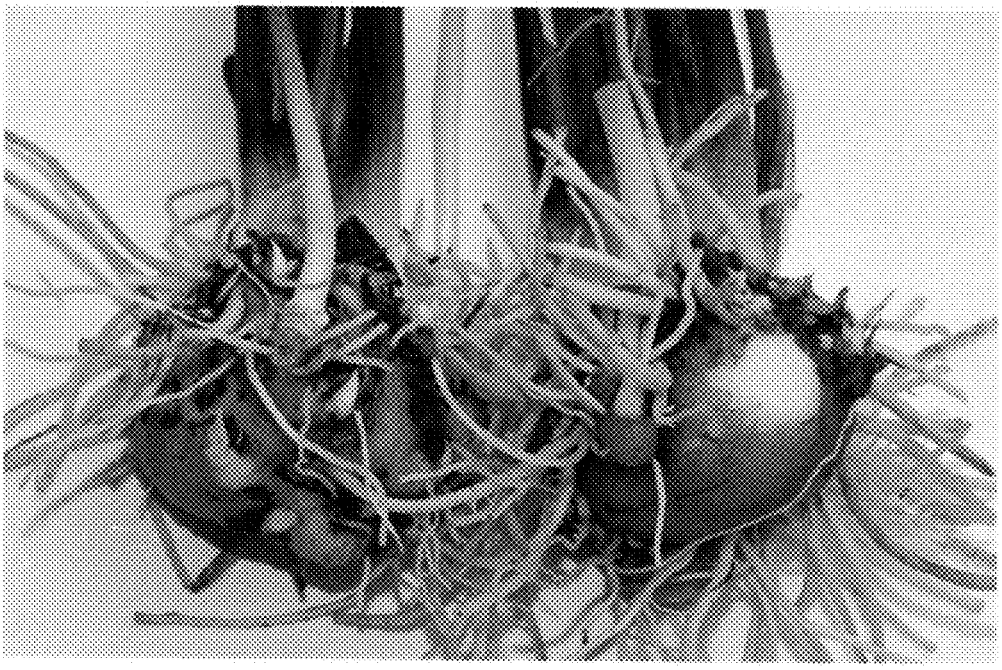

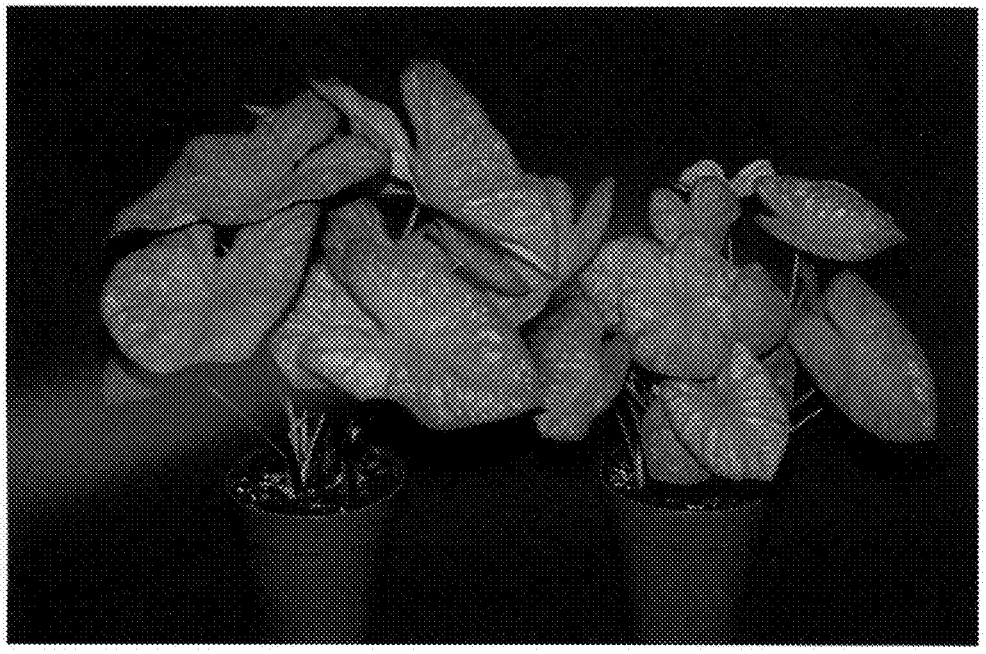

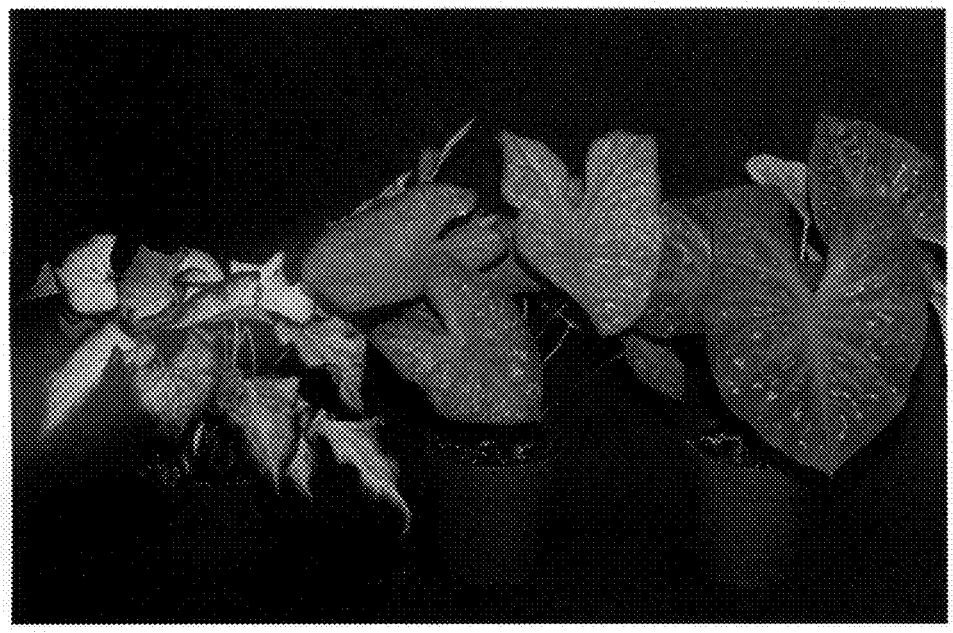
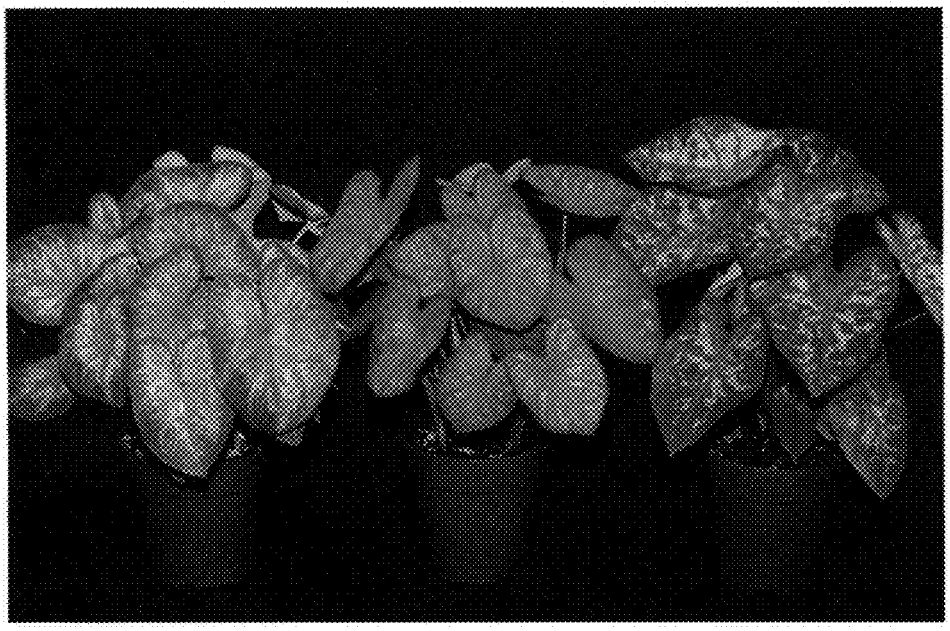

* * * * *